US009706152B2

(12) United States Patent
Griffith

(10) Patent No.: US 9,706,152 B2
(45) Date of Patent: Jul. 11, 2017

(54) REMOTE TRANSMISSION, MANIPULATION, AND DISPLAY OF INFRARED CAMERA DATA

(71) Applicant: General Electric Company, Schenectady, NY (US)

(72) Inventor: Katrina Marie Griffith, Melbourne, FL (US)

(73) Assignee: General Electric Company, Schenectady, NY (US)

( * ) Notice: Subject to any disclaimer, the term of this patent is extended or adjusted under 35 U.S.C. 154(b) by 612 days.

(21) Appl. No.: 14/085,079

(22) Filed: Nov. 20, 2013

(65) Prior Publication Data
US 2016/0227148 A1  Aug. 4, 2016

(51) Int. Cl.
*H04N 5/38* (2006.01)
*G01N 25/72* (2006.01)
(Continued)

(52) U.S. Cl.
CPC ............... *H04N 5/38* (2013.01); *F01D 21/12* (2013.01); *G01M 15/14* (2013.01); *G01N 25/72* (2013.01); *G06F 21/6263* (2013.01); *H04L 63/0428* (2013.01); *H04N 5/23203* (2013.01); *H04N 5/33* (2013.01); *H04N 7/22* (2013.01); *F05D 2260/80* (2013.01); *F05D 2260/821* (2013.01); *F05D 2270/11* (2013.01); *F05D 2270/8041* (2013.01); *H04N 5/2253* (2013.01); *H04N 5/2254* (2013.01); *H04N 5/2257* (2013.01);
(Continued)

(58) Field of Classification Search
CPC ........ H04N 5/38; H04N 7/22; H04N 5/23203; H04N 5/33; H04N 5/23293; H04N 5/2253; H04N 5/2257; H04N 2005/2255; H04N 5/2254; H04L 63/0428; G06F 21/6263; G01M 15/14
See application file for complete search history.

(56) References Cited

U.S. PATENT DOCUMENTS 4,930,861 A * 6/1990 Okabe ................ A61B 1/042
348/359
6,587,949 B1 * 7/2003 Steinberg ............... G06F 21/85
380/52
(Continued)

*Primary Examiner* — Sath V Perungavoor
*Assistant Examiner* — Philip Dang
(74) *Attorney, Agent, or Firm* — Eversheds-Sutherland (US) LLP

(57) ABSTRACT

Systems and methods for transmission, manipulation, and display of infrared camera (IR) data are provided. According to one embodiment of the disclosure, a system may include an IR camera associated with a gas turbine to acquire the IR data and an IR camera data acquisition server installed at a site associated with the gas turbine and communicatively coupled to the IR camera. The IR camera server is configured receive the IR data from the IR camera. An IR camera data processing server to classify the IR data into sensitive IR data and non-sensitive IR data based at least in part on predetermined criteria. Based at least in part on the non-sensitive IR data, images are generated. The images are provided via a user interface at the site associated with the gas turbine. The sensitive IR data is encrypted to produce encrypted sensitive IR data. The encrypted sensitive IR data and the non-sensitive IR data are transmitted to a processing center.

16 Claims, 7 Drawing Sheets

(51) Int. Cl.
*F01D 21/12* (2006.01)
*G01M 15/14* (2006.01)
*G06F 21/62* (2013.01)
*H04L 29/06* (2006.01)
*H04N 5/232* (2006.01)
*H04N 5/33* (2006.01)
*H04N 7/22* (2006.01)
*H04N 5/225* (2006.01)

(52) U.S. Cl.
CPC . *H04N 5/23293* (2013.01); *H04N 2005/2255* (2013.01)

(56) References Cited

U.S. PATENT DOCUMENTS

| | | | | |
|---|---|---|---|---|
| 7,851,758 | B1* | 12/2010 | Scanlon | G01J 5/02 250/330 |
| 8,126,197 | B2* | 2/2012 | Jones | G06K 9/036 382/100 |
| 8,242,445 | B1* | 8/2012 | Scanlon | G01J 5/02 250/330 |
| 8,261,064 | B2* | 9/2012 | Ditzman | G06F 21/83 178/18.01 |
| 8,316,237 | B1* | 11/2012 | Felsher | H04L 9/0825 380/282 |
| 8,413,493 | B1* | 4/2013 | Polywoda, III | G01M 15/14 73/112.01 |
| 2009/0254572 | A1* | 10/2009 | Redlich | G06Q 10/06 |
| 2010/0250497 | A1* | 9/2010 | Redlich | F41H 13/00 707/661 |
| 2013/0022202 | A1* | 1/2013 | Stroud | H04W 12/02 380/270 |
| 2013/0110775 | A1* | 5/2013 | Forsythe | G06F 17/30943 707/613 |
| 2013/0155227 | A1* | 6/2013 | Ferik | G01B 11/00 348/143 |
| 2013/0159021 | A1* | 6/2013 | Felsher | G06F 19/322 705/3 |
| 2013/0176418 | A1* | 7/2013 | Pandey | G01N 25/72 348/83 |
| 2013/0194379 | A1* | 8/2013 | Baleine | G02B 23/2492 348/36 |

* cited by examiner

REMOTE TRANSMISSION, MANIPULATION, AND DISPLAY OF INFRARED CAMERA DATA

TECHNICAL FIELD

This disclosure relates generally to data processing, and more particularly, to systems and methods for transmission, manipulation, and display of infrared camera data related to gas turbine operation.

BACKGROUND

Given the complexity and costs associated with modern industrial gas turbines, condition monitoring is becoming very important. A failure of gas turbine components or a shutdown due to malfunctioning can result in considerable expenses. Hot gas path parts such as, for example, turbine buckets can be monitored to determine their condition and assess remaining useful life. Timely discovery of any structural failures in the hot gas path parts may eliminate possible losses resulting from the gas turbine downtime.

Hot gas path parts can be monitored using infrared thermography. The infrared thermography may provide useful data for identifying defects and detecting areas for inspection as well as predicting maintenance schedule for the gas turbine, all while the gas turbine is in-service. However, data associated with infrared thermography may include sensitive information which is not intended for public use and may need to be securely transmitted and stored.

BRIEF DESCRIPTION OF THE DISCLOSURE

The disclosure relates to systems and methods for transmission, manipulation, and display of infrared (IR) camera data. According to one embodiment of the disclosure, a method is provided. The method may include receiving the IR data from an IR camera associated with a gas turbine at a site. The IR data may be classified as sensitive IR data and non-sensitive IR data based at least in part on predetermined criteria. Based at least in part on the non-sensitive IR data, images may be generated. The sensitive IR data may be encrypted. The encrypted sensitive IR data as well as the non-sensitive IR data may be transmitted to a remote processing center.

In another embodiment of the disclosure, a system is provided. The system may include an IR camera associated with a gas turbine to acquire the IR data and an IR camera data acquisition server installed at a site associated with the gas turbine and communicatively coupled to the IR camera, and an IR camera data processing server communicatively coupled to the IR camera data acquisition server. The IR camera data acquisition server may be configured to receive the IR data from the IR camera. The IR camera data processing server may be configured to classify the IR data into sensitive IR data and non-sensitive IR data based at least in part on predetermined criteria. Based at least in part on the non-sensitive IR data, images may be generated. The images may be provided via a user interface at the site associated with the gas turbine. The sensitive IR data may be encrypted to produce encrypted sensitive IR data. Both the encrypted sensitive IR data and the non-sensitive IR data may be transmitted to a processing center.

In yet another embodiment of the disclosure, another system for transmission of IR camera data is provided. The system may include an IR camera associated with a gas turbine to acquire the IR data, an IR camera data acquisition server installed at a site associated with the gas turbine and communicatively coupled to the IR camera, an IR camera data processing server installed at a site and communicatively coupled to the IR camera data acquisition server, and a remote processing center. The IR camera data acquisition server may be configured to receive the IR data from the IR camera. An IR camera data processing server may be configured to classify the IR data into sensitive IR data and non-sensitive IR data based at least in part on predetermined criteria. Based at least in part on the non-sensitive IR data, images may be generated. The images may be provided via a user interface at the site associated with the gas turbine. The sensitive IR data may be encrypted to produce encrypted sensitive IR data. The processing center may be configured to receive the encrypted sensitive IR data and the non-sensitive IR data. The sensitive IR data may comprise thermal information indicative of operational temperatures associated with the gas turbine and a scale for determining temperature gradients in the thermal information. Based at least in part on the scale and the encrypted non-sensitive IR data, the processing center may create enhanced views of the images.

Other embodiments and aspects will become apparent from the following description taken in conjunction with the following drawings.

DETAILED DESCRIPTION

Figure 1:
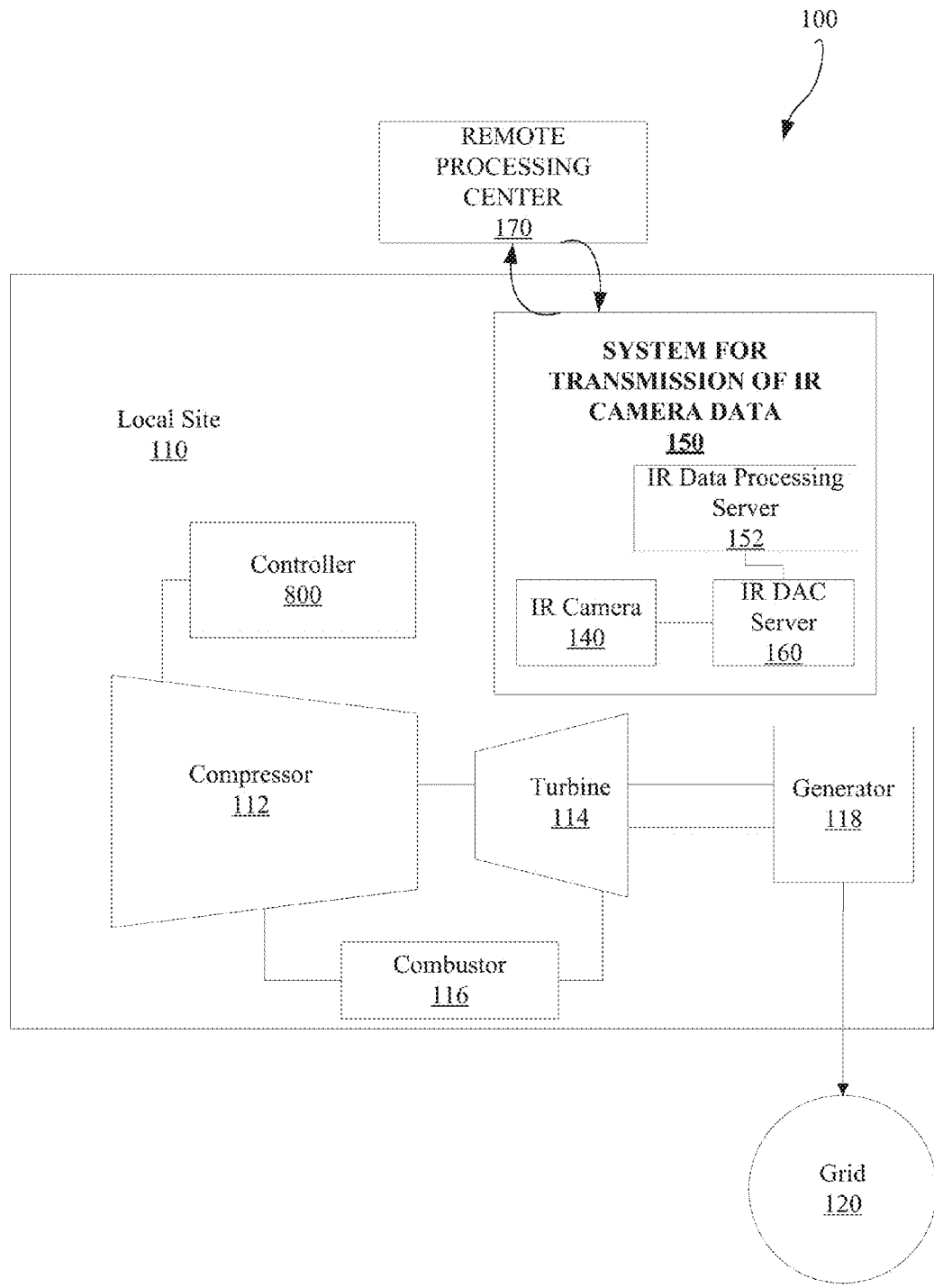
FIG. 1 is a block diagram illustrating an example environment and system for transmission of IR camera data, in accordance with an embodiment of the disclosure.

The following detailed description includes references to the accompanying drawings, which form part of the detailed description. The drawings depict illustrations, in accordance with example embodiments. These example embodiments, which are also referred to herein as "examples," are described in enough detail to enable those skilled in the art to practice the present subject matter. The example embodiments may be combined, other embodiments may be utilized, or structural, logical, and electrical changes may be made, without departing from the scope of the claimed subject matter. The following detailed description is, therefore, not to be taken in a limiting sense, and the scope is defined by the appended claims and their equivalents.

Certain non-limiting embodiments described herein relate to systems and methods for transmission, manipulation, and display of IR data associated with a gas turbine. A gas turbine can include a compressor, a combustor, and turbine sections. The compressor and the combustor can produce pressured gas transmitted to the turbine section where the gas is converted to mechanical energy. The turbine section can include several stages, typically three, each of which can include a nozzle and a wheel with corresponding buckets. Buckets can include rotating surfaces encountering hot gases received from the compressor. The buckets can be affected by operating conditions of the gas turbine, for example, high temperatures, high pressures, high-speed rotations, and so forth. As a result, the buckets can be subject to failures caused by oxidation and other conditions, such as creep, fatigue, degradation, and so forth. Even though example embodiments are described with reference to turbine buckets, it should be understood that the technology disclosed herein is not limited to the turbine buckets and can be utilized with other hot gas path parts of a gas turbine.

Unexpected failures of buckets are typically associated with increased maintenance costs; moreover, the damaged parts may cause the gas turbine to become nonoperational. It may be difficult to assess bucket condition and predict its remaining useful life while the gas turbine is in service. However, several methods, such as, for example, infrared thermography, may be used to monitor bucket health.

The infrared thermography may involve an infrared camera positioned in the turbine section to capture infrared data showing temperature patterns of blades in a bucket. Data from the infrared camera can be analyzed to identify defects in the gas turbine blades based at least in part on a temperature distribution. Thus, monitoring bucket health may provide useful information related to the state of the blades of the bucket and potential areas for inspection. Using this information, premature bucket failure can be prevented. However, the data from the infrared camera can include thermal information indicative of operational temperatures of the turbine. This information may be sensitive and, as such, may need to be secured.

According to the methods and systems disclosed herein, the IR camera data may be analyzed and sensitive data may be identified based at least in part on predefined criteria. The sensitive IR data may be extracted and encrypted for transmission to a remote storage location. The sensitive IR data may include thermal information that may be used to determine operating temperatures of the gas turbine.

The non-sensitive IR data may be processed locally to generate images representing bucket health. These images may be provided to a customer operating the gas turbine at the local site, for example, via a web service. The customer may use the images to identify defects and areas for future inspection.

Non-sensitive IR data as well as the encrypted sensitive IR data may be transmitted to a remote processing center. The processing center may generate enhanced images depicting bucket condition based at least in part on both sensitive and non-sensitive data. The enhanced images may visualize health analytics associated with the gas turbine.

The processing center may perform additional calculations based at least in part on the sensitive and non-sensitive data and further data received from sensors associated with the gas turbine. The calculations may be used to predict a maintenance schedule of the gas turbine hot gas path components.

The technical effects of certain embodiments of the disclosure may include securing sensitive data associated with gas turbine operation while providing information for assessing bucket condition and remaining useful life. Further technical effects of certain embodiments of the disclosure may include secure collecting of the sensitive data in a central storage for further analysis and processing.

The following provides the detailed description of various example embodiments related to systems and methods for transmission of IR camera data.

Referring now to FIG. 1, a block diagram illustrates an example system environment 100 suitable for implementing methods and systems for transmission of IR camera data, in accordance with one or more example embodiments. In particular, the system environment 100 may include a local site 110 associated with a gas turbine assembly including a compressor 112, a turbine 114 coupled to the compressor 120, and a combustor 116. The turbine 114 may drive a generator 118 that produces electrical power and supplies the electrical power via a breaker to an electrical grid 120.

An IR camera 140 may be associated with the turbine 114. For example, the IR camera 140 may be installed on the outer covering above a stage 1 bucket. In other embodiments, the IR camera 140 may be installed in other locations on the turbine 140 or otherwise. The IR camera 140 may be a component of a system 150 for transmission of IR camera data and may transfer data captured from the turbine 140 to other component of the system 150. For example, the IR camera 140 may transfer the data to an IR data acquisition server 160. An IR camera data processing server 152 may be responsible for data sensitivity delineation, and sensitive data encryption. In some embodiments, the data communicated to the may include non-sensitive data only.

The system 150 may differentiate the data into sensitive and non-sensitive and provide non-sensitive data to a customer associated with the local site 110. Additionally, the system 150 may transmit the sensitive and non-sensitive data to a remote processing center 170 securely. Though the processing center 170 is shows as a separate component, in some embodiments of the disclosure, the processing center 170 may be a component of the system for transmission of IR data 150.

The compressor 112, turbine 114, and combustor 116 may be coupled to the controller 800 managing the operations of the gas turbine. The controller 800 may include a computer system having a processor(s) that executes programs for controlling the operations of the gas turbine using sensor inputs, transfer function outputs and instructions from human operators.

Figure 2:
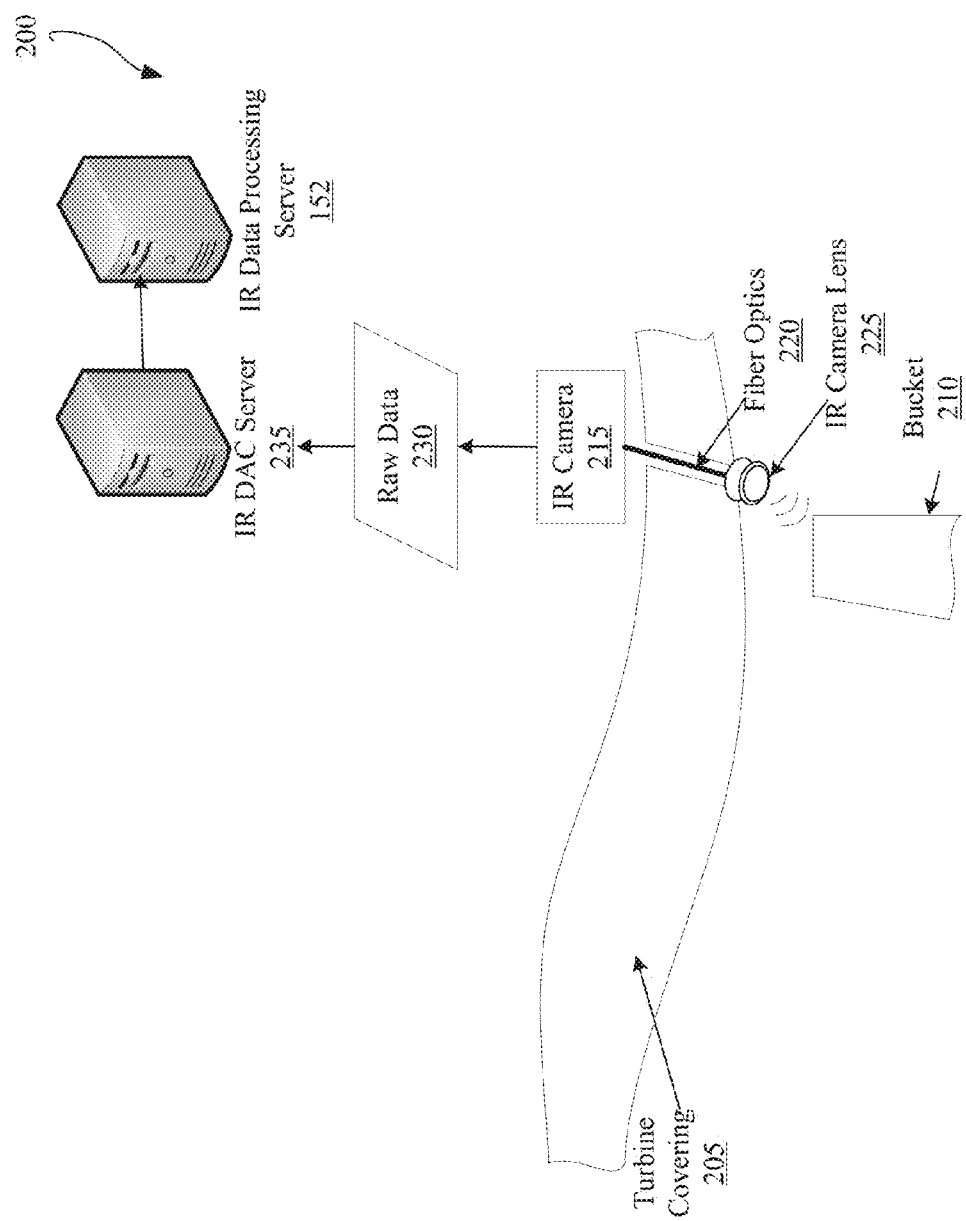
FIG. 2 illustrates an example positioning of an IR camera and its components on a turbine and capturing of IR data, in accordance with a non-limiting embodiment of the disclosure.

FIG. 2 illustrates an example positioning 200 of IR camera and corresponding components on a turbine and capturing of IR data, in accordance with an embodiment of the disclosure. To install the IR camera 140, a hole may be drilled into a turbine covering 205. In the hole, fiber optic components 220 with an IR camera lens 225 may be installed. The IR camera lens 225 may be positioned to view a bucket 210 of the turbine. The fiber optics 220 may connect with an IR camera 215 to transmit data from the IR camera lens 225 to the IR camera 215. The IR camera 215 may be positioned outside the turbine with only the IR camera lens 225 and the fiber optics 220 exposed to the operational gas.

The IR camera 215 may capture the temperature distribution of the bucket 210 surface. In some embodiments, the IR camera 215 may be set up to run at particular intervals. Raw data 230 generated by the IR camera 215 may be transmitted to an IR server 235. The IR server 235, as a part of the system for transmission of IR camera data 150, may process the received raw data 230 to determine sensitive data. For example, the sensitive data may include formal thermal information, such as a scale which may be used to determined operational temperatures of the turbine. The IR server 235 may further ensure providing non-sensitive data to a customer and secure transmission of the sensitive data to the operational center. These and other operations related to IR camera 215 data are be described in further detail with reference to FIGS. 6 and 7 below.

Figure 3:
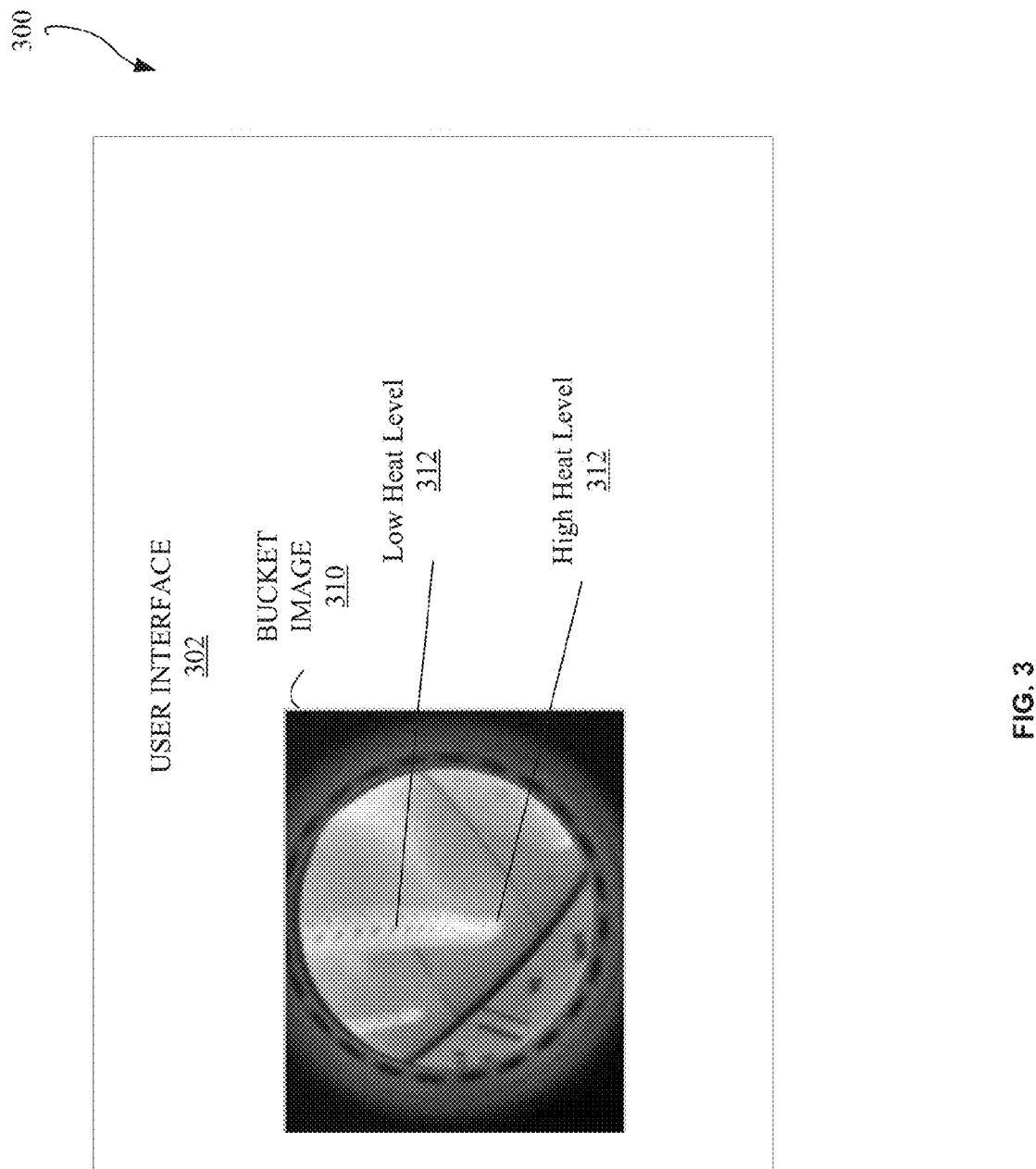
FIG. 3 depicts a user interface providing an example bucket image based at least in part on non-sensitive IR data, in accordance to an embodiment of the disclosure.

Returning now to FIG. 2, the non-sensitive data may be extracted from the raw data 230 by the IR server 235. Using non-sensitive data, the IR server 235 may generate images representing bucket conditions. The images may be generated for each blade of the bucket 210 and may be provided to a customer for examination. The images may be provided via a user interface 302 as illustrated by FIG. 3. For example, a bucket image 310 may be black and white. The brightness of the bucket image 310 may indicate levels of heat. For example, dark areas may represent bucket sections with a low heat level 312 and light areas may indicate sections with a high heat level 312. Thus, an operator may identify portions of a blade with a higher heat level in comparison to the rest of the blade. This may facilitate estimating remaining service life of the bucket and prevent or otherwise minimize bucket failures caused by cracks, flaws, fractures, and so forth.

The black and white bucket image 310 includes pixels of varying brightness corresponding to changes in temperature but without a scale indicative of actual temperature gradients. Thus, the data associated with the bucket image 310 may be classified as non-sensitive. In some example embodiments, the bucket image 310 may include an image in the GIFF format.

Figure 4:
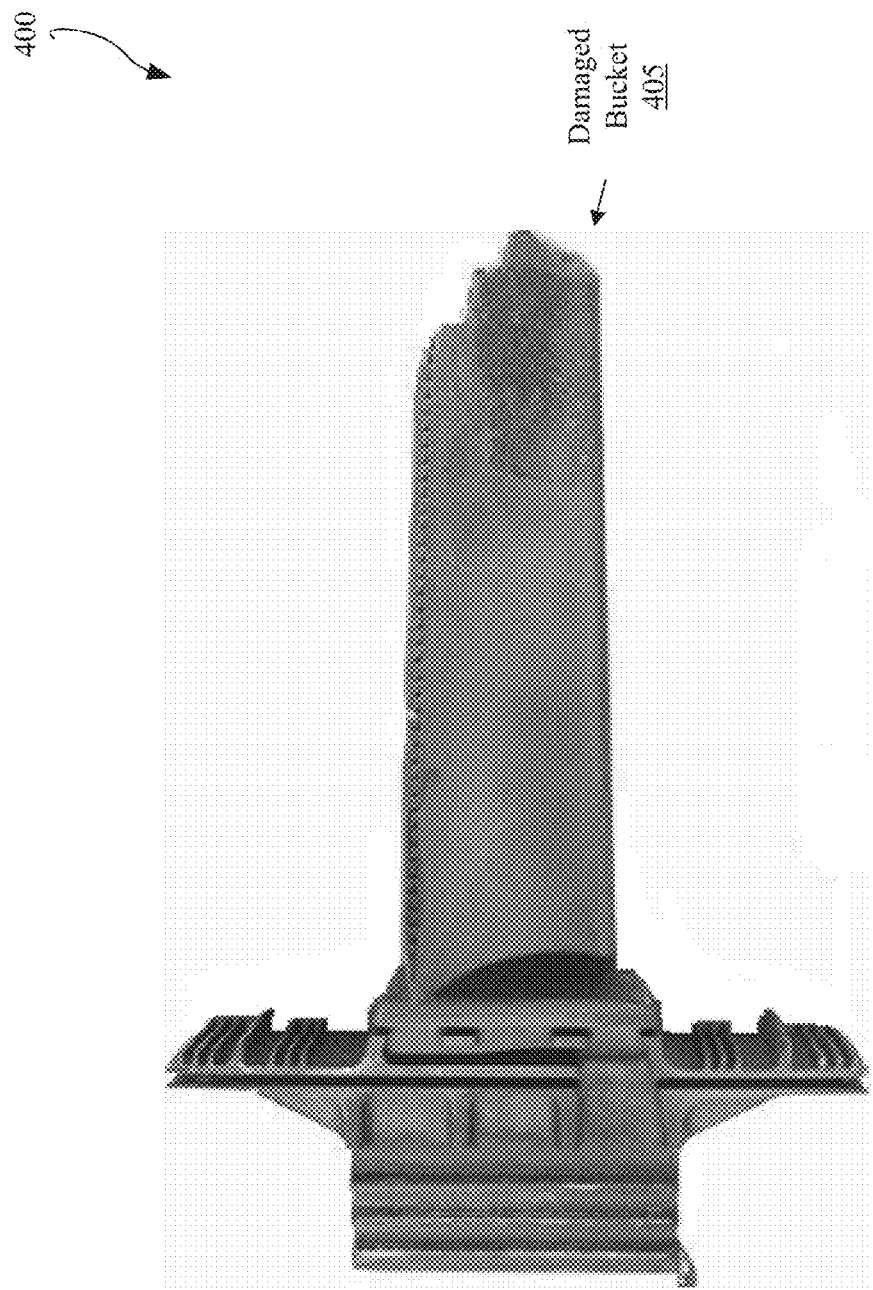
FIG. 4 depicts an example damaged bucket, in accordance with an embodiment of the disclosure.

FIG. 4 depicts an example representation 400 of a damaged bucket 405 which may be a result of an oxidation process. The oxidation may be induced, for example, by the presence of contaminants, such as sulfur, vanadium, sodium and potassium salts, and/or lead, in the hot gas environment. Hot oxidation may accelerate degradation of the coating layer and the base metal of the gas turbine bucket eventually producing defects in the coating and the base metal leading to bucket failures. The defects in the coating may be associated with higher heating patterns which may be captured by an IR camera.

Figure 5:
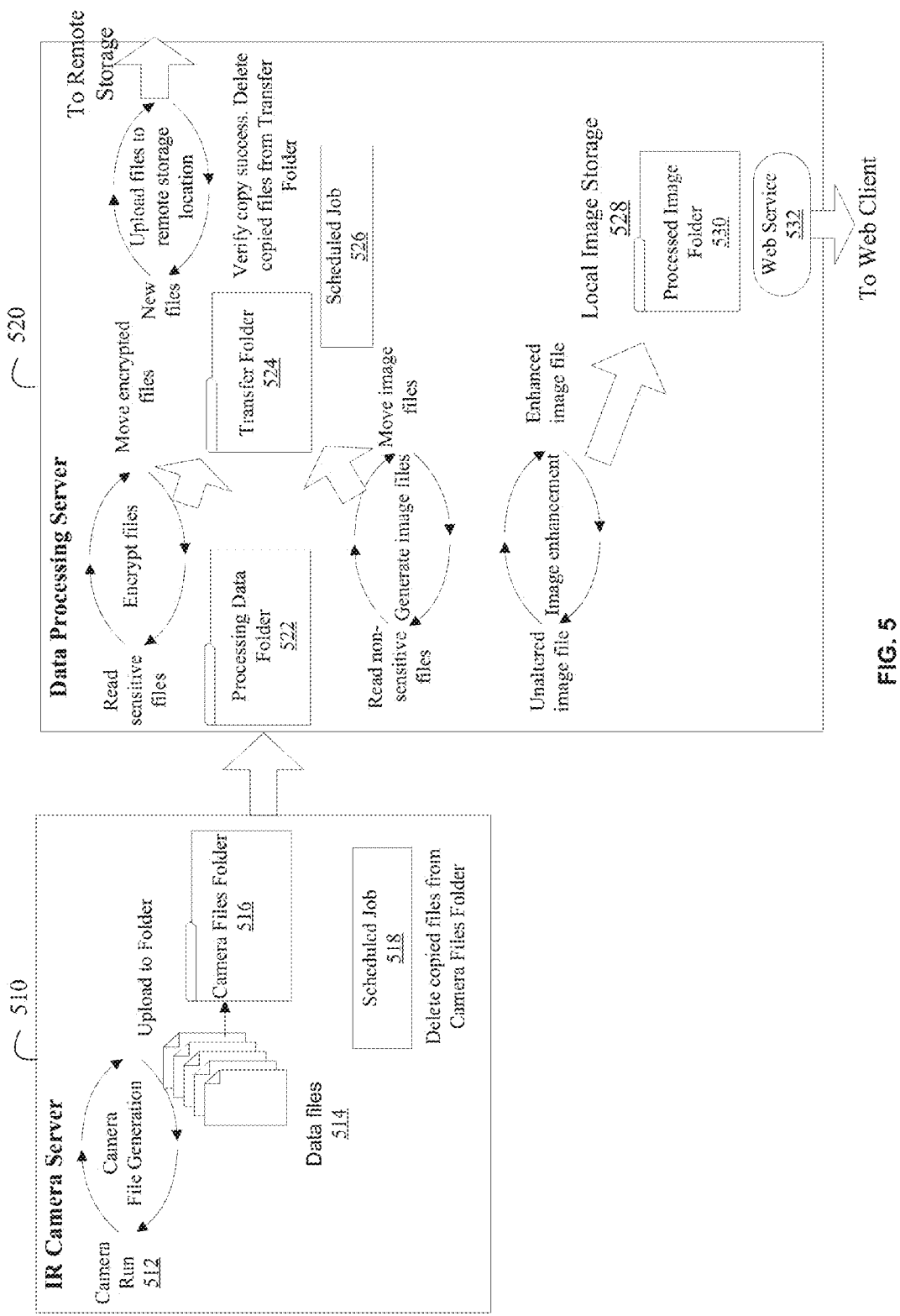
FIG. 5 is a block diagram illustrating processing of raw data from the IR camera site associated with the gas turbine, in accordance with an embodiment of the disclosure.

FIG. 5 is a block diagram illustrating processing of raw data from the IR camera in a local site associated with the gas turbine, in accordance with an example embodiment of the disclosure. Raw data from the IR camera run 512 may be received by an IR camera server 510. The IR camera server 510 may also be located at the local site. The IR camera server 510 includes a data acquisition machine that may be hardwired to the IR camera. When the IR camera is triggered, the raw data may be transmitted to IR camera server 510 that processes the raw data into a set of data files 514.

The files 514 may be generated based at least in part on a particular configuration for the IR camera for a particular bucket. For each bucket, the IR camera may be configured to take N photos in a camera run. For example, the IR camera may capture 45 photos in 10 seconds or less for bucket 1, 45 pictures for bucket 2, 45 pictures for bucket 3, and so on. The images and the data may be included in files 514 and stored per camera run 512, and per bucket. When the camera run 512 is completed, the files 514 may be removed from the IR camera server 510 and sent to a data processing server 520 and further into a processing data folder 522. Copies of the files in the camera files folder 516 may be deleted by a scheduled job 518.

The data processing server 520 may separate the sensitive data from the non-sensitive data. If determined to be sensitive, the files 514 may be encrypted. In various embodiments, the encryption may be performed using various encryption techniques and the level of the encryption may be configurable. For example, encryption libraries from Java may be used for this purpose. Alternatively, stronger encryption may be used, for example, using Bouncy Castle or similar tools.

After being encrypted, the files may be ready for a transfer folder 524. Non-sensitive files can be moved/copied directly to the transfer folder 524. Additionally, the non-sensitive files can be read to generate image files. For example, the image files may be saved in the GIFF format. Image files may be enhanced and transmitted to a local image storage 528 and further into a processed image folder 530. In the processed image folder 530, a limited set of non-sensitive files may be kept for review by the customer. A periodic reuse of the files may be performed, for example, based at least in part on a size. In some embodiments, the data may be kept, for example, for 6 months and then overwritten.

The images in the processed image folder 530 may be accessed through a web server 532 by a web client. The customer can view the images using a user interface associated with the web client. Data in the transfer folder 524 (a scheduled job 526) can be transferred to a remote storage location associated with a processing center. To transfer data between the local site and the remote site, a Transmission Control Protocol/Internet Protocol (TCP/IP) protocol may be used. After the files are transferred, operation success may be verified and copies of the successfully transferred files may be removed from the transfer folder 524.

Figure 6:
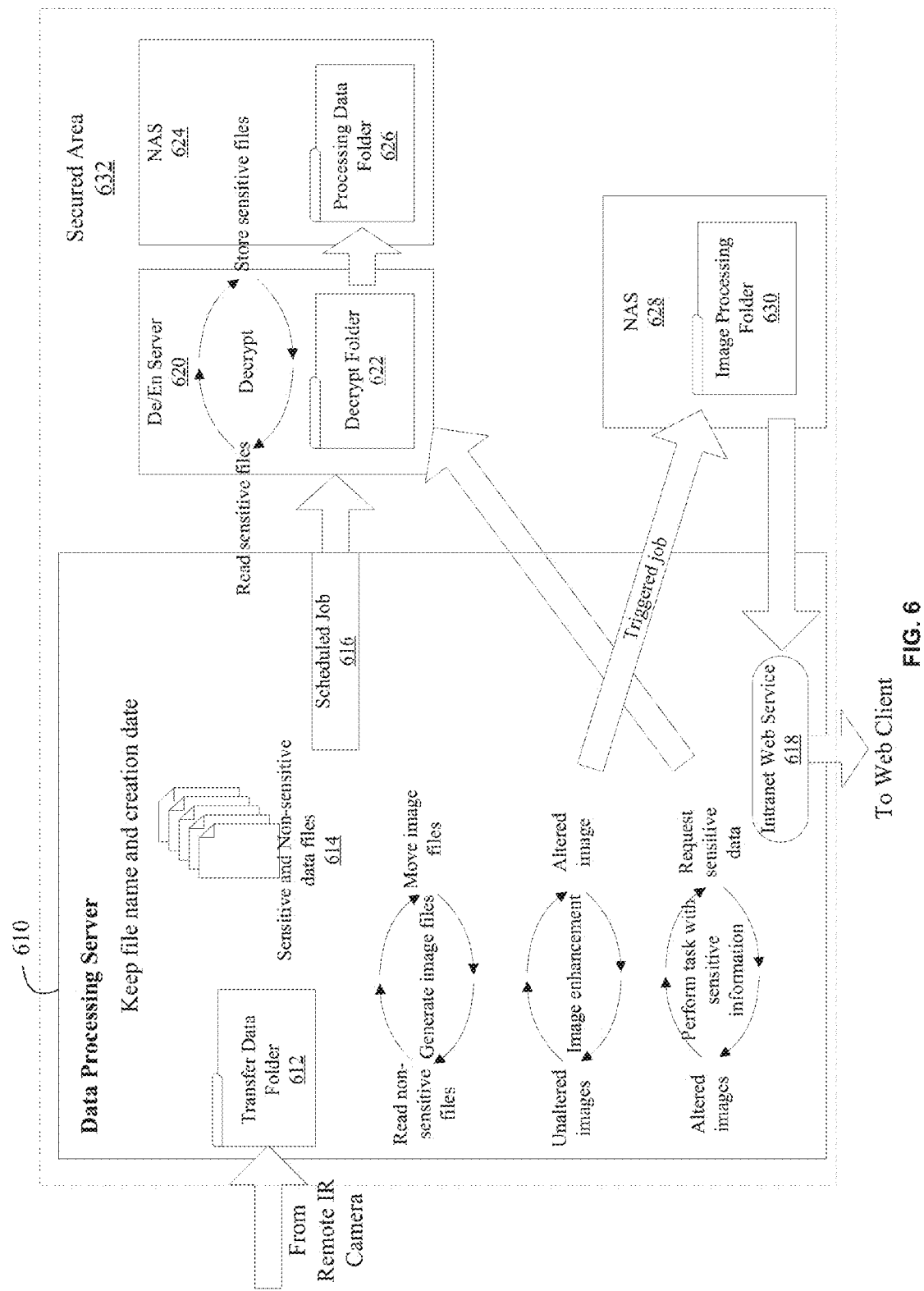
FIG. 6 is a block diagram illustrating processing of IR camera data at a remote site, in accordance with an embodiment of the disclosure.

FIG. 6 is a block diagram illustrating processing of IR camera data at the remote site, in accordance with an example embodiment of the disclosure. Since the IR camera data transmitted to the processing center can include both sensitive and non-sensitive data, processing of the IR camera data may be performed in a secured area 632. Once the IR camera data is received from the customer local site associated with the gas turbine, both the sensitive and non-sensitive data may be used to create enhanced images. The sensitive and non-sensitive data may also be used for other purposes, such as, health analytics, assessing remaining life of the bucket and so forth. The data may be received by a data processing server 610 of the processing center and stored in the transfer data folder 612. The data may include sensitive and non-sensitive data files 614.

The sensitive data may be preliminary moved to a decrypt folder 622 and decrypted by Decrypt/Encrypt (De/En) server 620 using a scheduled job 616. The decrypted files may be stored to a processing data folder 626 on a Network Access Server (NAS) 624.

The non-sensitive files may be used to generate images similarly to the image generation processes utilized at the local site. The images generated at the local site may not be transmitted because the images are larger than raw image information. Therefore, the images may be regenerated at the processing center. The generated images may be black and white with brightness indicative of heat levels associated with various portions of the bucket. These images may be stored to an image processing folder 630 on NAS 630 to be accessed through an Intranet Web Service 618 by a processing center expert.

The images may be provided to the expert so that the expert can see the same images as the customer. However, in addition to the information available to the customer, the images may be processed using the sensitive data to produce enhanced images and enhanced analytics. Enhancing the images may include a variety of attributes not necessarily visual in nature. Some attributes, however, can be visual, for example, an enhanced view with the appropriate scale for the temperature gradients can be provided. The enhanced view can be analyzed and used by experts associated with the operating center. Additionally, some calculations may be performed and results of the calculations may be used along with additional measurements made by other sensors to generate bucket state trends, forecasts, maintenance plans, and so forth. The enhanced images may allow determining how long a particular bucket in stage 1 or other stages can function before any maintenance is needed. The enhanced images may be provided to the expert via the intranet web service 618 though the web user interface.

Figure 7:
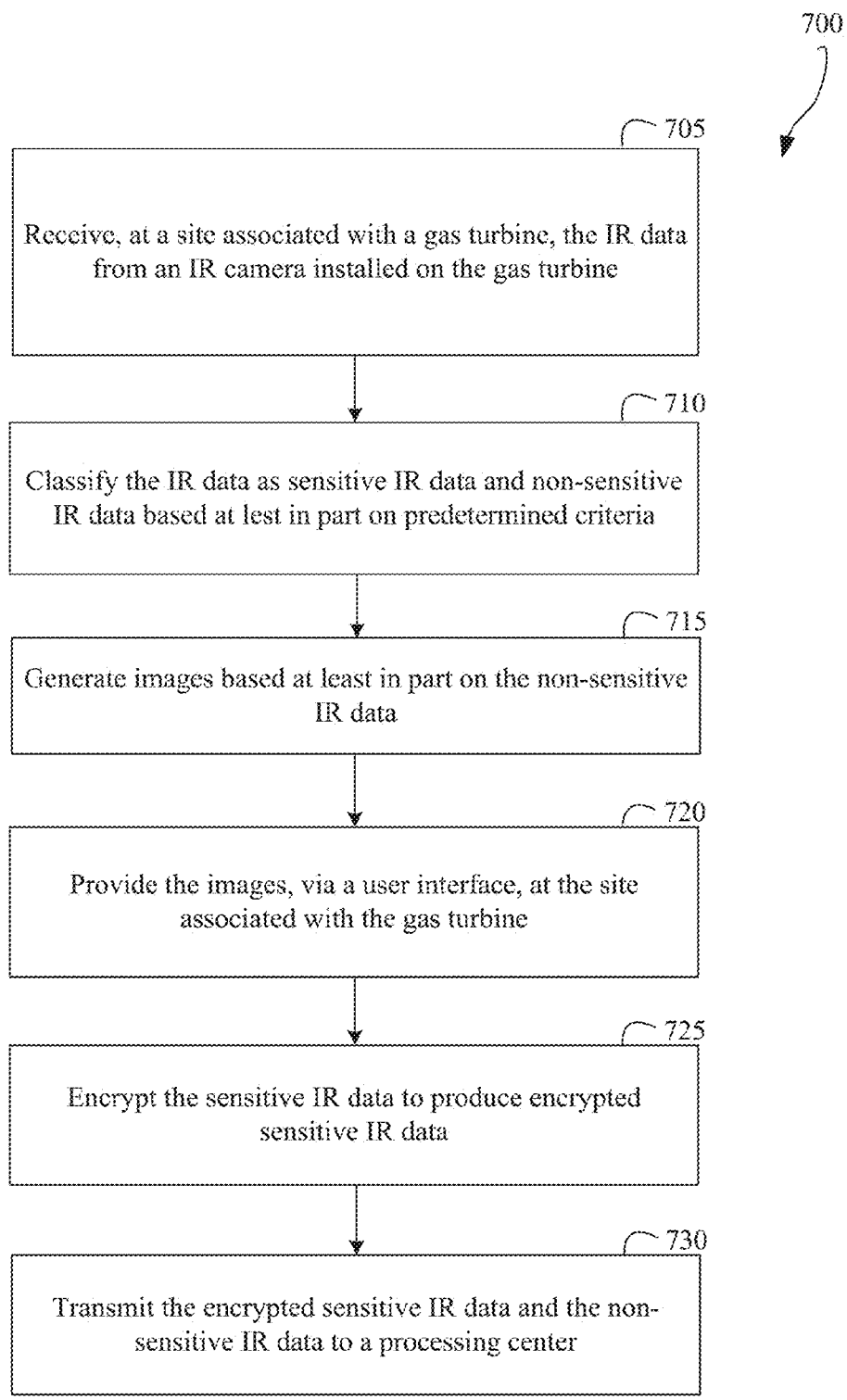
FIG. 7 depicts a process flow diagram illustrating an example method for transmission of infrared camera data, in accordance with an embodiment of the disclosure.

FIG. 7 depicts a process flow diagram illustrating an example method 700 for transmission of infrared camera data, in accordance with an embodiment of the disclosure. The method 700 may be performed by processing logic that may include hardware (e.g., dedicated logic, programmable logic, and microcode), software (such as software run on a general-purpose computer system or a dedicated machine), or a combination of both. In one example embodiment, the processing logic resides in a user device or a server. Alternatively, the processing logic may reside, partially or in whole, at local or remote servers or other locations. It will be appreciated by one of ordinary skill in the art that instructions said to be executed by the user device or the server may, in fact, be retrieved and executed by one or more processors. The user device or the server may also include memory cards, servers, and/or computer discs. Although the user device or the server may be configured to perform one or more steps described herein, other units may be utilized while still falling within the scope of various embodiments.

As shown in FIG. 7, the method 700 may commence in operation 705 with receiving IR data from an IR camera associated with a gas turbine. For example, the IR camera may be positioned on the outer covering of the gas turbine, while an IR lens may be installed inside the turbine (e.g. stage 1 bucket) to capture bucket blades in operational conditions. The IR camera and the IR lens may be connected by fiber optics components. The IR camera may run at a particular interval and take a predefined number of photos in a camera run. The series of photos captured by the IR camera may represent temperature pattern of each blade in a bucket. The IR data may be received locally, at a site associated with the gas turbine.

At operation 710, the IR data may be classified as sensitive or non-sensitive IR data based at least in part on predefined criteria. In some embodiments, sensitive information may include thermal information, such as temperature gradients indicative of operating temperatures of the turbine. As a result of IR data classifying a set of files may be created. Each file may contain a predetermined number of images associated with the turbine bucket.

The non-sensitive IR data may be used to generate images representing temperature distribution of the bucket at operation 715. The images may be black and white heat maps. By representing heat levels of the bucket through brightness, the images do not include a scale and, therefore, cannot be used to find out operating temperatures of the turbine. The generated images including non-sensitive information may be provided, via a user interface, at the site associated with the turbine at operation 720.

At operation 725, IR data classified as sensitive may be encrypted. Encryption may be performed using, for example, default Java encryption libraries. Alternatively, third party solutions may be used (for example, Bouncy Castle). The encrypted sensitive IR data and non-sensitive IR data may be transmitted to a processing center at operation 730. The processing center may decrypt the sensitive data and generate enhanced images using both sensitive and non-sensitive data. The enhanced images may include a scale for determining temperature gradients associated with the bucket and may be used to identify areas for inspection and visualize health analytics associated with the gas turbine.

Additionally, the processing center may receive data sensed and measured by one or more sensors installed associated with the gas turbine and/or calculated by the controller 800. The data may include an inlet temperature, airflow, fuel flow, inlet pressure, exhaust pressure, exhaust temperature, compressor discharge pressure, compressor discharge temperature, turbine power, ambient pressure, humidity, field manifold pressure, exhaust ignition, contaminants detected in the fuel or environment, and so forth.

Using the aforementioned data, the processing center may perform additional calculations to predict maintenance schedule of the gas turbine in general and the bucket captured by the IR camera, in particular.

Accordingly, certain embodiments described herein can provide data for monitoring of turbine health during turbine operation while keeping confidentiality of sensitive data related to thermal information of the gas turbine operation. The disclosed methods and systems may encrypt sensitive data and securely transmit it to an operational center for processing, modeling, and display.

References are made to block diagrams of systems, methods, apparatuses, and computer program products according to example embodiments. It will be understood that at least some of the blocks of the block diagrams, and combinations of blocks in the block diagrams, may be implemented at least partially by computer program instructions. These computer program instructions may be loaded onto a general purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the block or blocks.

One or more components of the systems and one or more elements of the methods described herein may be implemented through an application program running on an operating system of a computer. They also may be practiced with other computer system configurations, including hand-held devices, multiprocessor systems, microprocessor based or programmable consumer electronics, mini-computers, mainframe computers, and the like.

Application programs that are components of the systems and methods described herein may include routines, programs, components, data structures, and so forth that implement certain abstract data types and perform certain tasks or actions. In a distributed computing environment, the application program (in whole or in part) may be located in local memory or in other storage. In addition, or alternatively, the application program (in whole or in part) may be located in remote memory or in storage to allow for circumstances where tasks are performed by remote processing devices linked through a communications network.

Many modifications and other embodiments of the example descriptions set forth herein to which these descriptions pertain will come to mind having the benefit of the teachings presented in the foregoing descriptions and the associated drawings. Thus, it will be appreciated that the disclosure may be embodied in many forms and should not be limited to the example embodiments described above.

Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for transmission of infrared camera (IR) data, the method comprising:
   receiving, at a site associated with a gas turbine, the IR data from an IR camera associated with the gas turbine;
   identifying, based on the IR data, thermal information indicative of operational temperatures associated with the gas turbine;
   based on the identifying, classifying the thermal information as sensitive data to be processed at a secure processing area, the secure processing area being remote with respect to the site associated with the gas turbine;
   based on the classifying, extracting the sensitive data from the IR data to obtain extracted sensitive IR data;
   classifying non-extracted data of the IR data as non-sensitive IR data;
   generating images based at least in part on the non-sensitive IR data;
   providing the images, via a user interface, at the site associated with the gas turbine;
   encrypting the extracted sensitive IR data to produce encrypted sensitive IR data, wherein the encrypting of the extracted sensitive IR data includes encrypting a scale for determining temperature gradients in the thermal information; and
   transmitting the encrypted sensitive IR data and the non-sensitive IR data to the processing center.

2. The method of claim 1, further comprising installing the IR camera on an outer covering of the gas turbine and installing an IR camera lens inside the gas turbine, the IR camera being connected to the IR camera lens through a fiber optics component.

3. The method of claim 1, wherein the generating the images comprises generating pixels with brightnesses corresponding to levels of heat.

4. The method of claim 1, further comprising creating enhanced views of the images based at least in part on the scale and the non-sensitive IR data.

5. The method of claim 4, further comprising:
   performing additional calculations based at least in part on further data received from one or more sensors associated with the gas turbine; and
   based at least in part on the additional calculations, predicting maintenance schedule of the gas turbine.

6. The method of claim 4, further comprising displaying the enhanced views of the images to visualize health analytics associated with the gas turbine.

7. The method of claim 1, wherein the classifying of the IR data comprises creating a set of files, each file comprising a predetermined number of images associated with a turbine bucket.

8. A system for transmission of infrared camera (IR) data, the system comprising:
   an IR camera associated with a gas turbine to acquire the IR data; and
   an IR camera server installed at a site associated with the gas turbine and communicatively coupled to the IR camera, the IR camera data acquisition server being configured to:
   receive the IR data from the IR camera;
   identify, based on the IR data, thermal information indicative of operational temperatures associated with the gas turbine;
   based on the thermal information indicative of operational temperatures, classify the thermal information as sensitive data to be processed at a secure processing area, the secure processing area being remote with respect to the site associated with the gas turbine;
   based on the sensitive data classified to be processed at a secure processing area, extract the sensitive data from the IR data to obtain extracted sensitive IR data;
   classify non-extracted data of the IR data as non-sensitive IR data;
   generate images based at least in part on the non-sensitive IR data;
   provide the images, via a user interface, at the site associated with the gas turbine;
   encrypt the extracted sensitive IR data to produce encrypted sensitive IR data, wherein the encrypting of the extracted sensitive IR data includes encrypting a scale for determining temperature gradients in the thermal information; and
   transmit the encrypted sensitive IR data and the non-sensitive IR data to the processing center.

9. The system of claim 8, wherein the IR camera is installed on an outer covering of the gas turbine and an IR camera lens is installed inside the gas turbine, the IR camera being connected to the IR camera lens through a fiber optics component.

10. The system of claim 8, wherein the images comprise pixels with brightnesses corresponding to levels of heat.

11. The system of claim 8, wherein the processing center is operable to create enhanced views of the images based at least in part on the scale and the non-sensitive IR data.

12. The system of claim 11, wherein the processing center is operable to perform additional calculations based at least in part on further data received from one or more sensors associated with the gas turbine and, based at least in part on the calculations, predict maintenance schedule of the gas turbine.

13. The system of claim 12, wherein the processing center is operable to display the enhanced views of the images to visualize health analytics associated with the gas turbine.

14. The system of claim 13, wherein the classifying of the IR data comprises creating a set of files, each file comprising a predetermined number of images associated with a turbine bucket.

15. The system of claim 8, wherein the IR data is acquired at predetermined intervals.

16. A system for transmission of infrared camera (IR) data, the system comprising:
- an IR camera associated with a gas turbine to acquire the IR data;
- an IR camera server installed at a site associated with the gas turbine and communicatively coupled to the IR camera, the IR camera data acquisition server being configured to:
  - receive the IR data from the IR camera;
  - identify, based on the IR data, thermal information indicative of operational temperatures associated with the gas turbine;
  - based on the thermal information indicative of operational temperatures, classify the thermal information as sensitive data to be processed at a secure processing area, the secure processing area being remote with respect to the site associated with the gas turbine;
  - based on the thermal information classified as sensitive data to be processed at a secure processing area, extract the sensitive data from the IR data to obtain extracted sensitive IR data;
  - classify non-extracted data of the IR data as non-sensitive IR data;
  - generate images based at least in part on the non-sensitive IR data;
  - provide the images, via a user interface, at the site associated with the gas turbine; and
  - encrypt the extracted sensitive IR data to produce encrypted sensitive IR data, wherein the encrypting of the extracted sensitive IR data includes encrypting a scale for determining temperature gradients in the thermal information; and
- a processing center configured to:
  - receive the encrypted sensitive IR data and the non-sensitive IR data, wherein the encrypting of the extracted sensitive IR data includes encrypting a scale for determining temperature gradients in the thermal information; and
  - create enhanced views of the images based at least in part on the scale and the encrypted non-sensitive IR data.

* * * * *